United States Patent [19]

Abela

[11] Patent Number: 5,895,400
[45] Date of Patent: Apr. 20, 1999

[54] CATHETER WITH BRISTLES

[76] Inventor: George S. Abela, 6201 Windrush Lane, E. Lansing, Mich. 48823

[21] Appl. No.: 08/884,085

[22] Filed: Jun. 27, 1997

[51] Int. Cl.$^6$ .................................................. A61B 17/00
[52] U.S. Cl. ................................................................. 606/159
[58] Field of Search ............................... 606/1, 159, 170, 606/171, 180; 15/72, 104.14

[56] References Cited

U.S. PATENT DOCUMENTS

| | | |
|---|---|---|
| 4,445,509 | 5/1984 | Auth . |
| 4,646,736 | 3/1987 | Auth . |
| 4,850,957 | 7/1989 | Summers . |
| 4,867,156 | 9/1989 | Stack et al. . |
| 4,990,134 | 2/1991 | Auth . |
| 5,009,659 | 4/1991 | Hamlin et al. ........................... 606/159 |
| 5,059,211 | 10/1991 | Stack et al. . |
| 5,303,719 | 4/1994 | Wilk et al. ............................... 606/159 |
| 5,306,286 | 4/1994 | Stack et al. . |
| 5,314,407 | 5/1994 | Auth et al. . |
| 5,364,393 | 11/1994 | Auth et al. . |
| 5,370,653 | 12/1994 | Cragg . |
| 5,681,335 | 10/1997 | Serra et al. ............................... 606/159 |

*Primary Examiner*—Michael Buiz
*Assistant Examiner*—William W. Lewis
*Attorney, Agent, or Firm*—William L. Feeney; Kerkam, Stowell, Kondracki & Clarke, P.C.

[57] ABSTRACT

A system and method removes material from the wall of a passage, such as a vein or artery, in a patient's body with a series of bristles that are rotated. The bristles are part of a sweep catheter having a proximal end and a distal end with a tip thereon. Bristles next to the tip extend out from the distal end a shorter distance than the bristles further from the tip. The bristles, which have smaller bristles or sub-bristles thereon, are inclined away from the tip as they extend out from the distal end of the sweep catheter. The bristles push removed materials away from the tip and towards a suction channel of a guide catheter whereby the materials are removed.

20 Claims, 1 Drawing Sheet

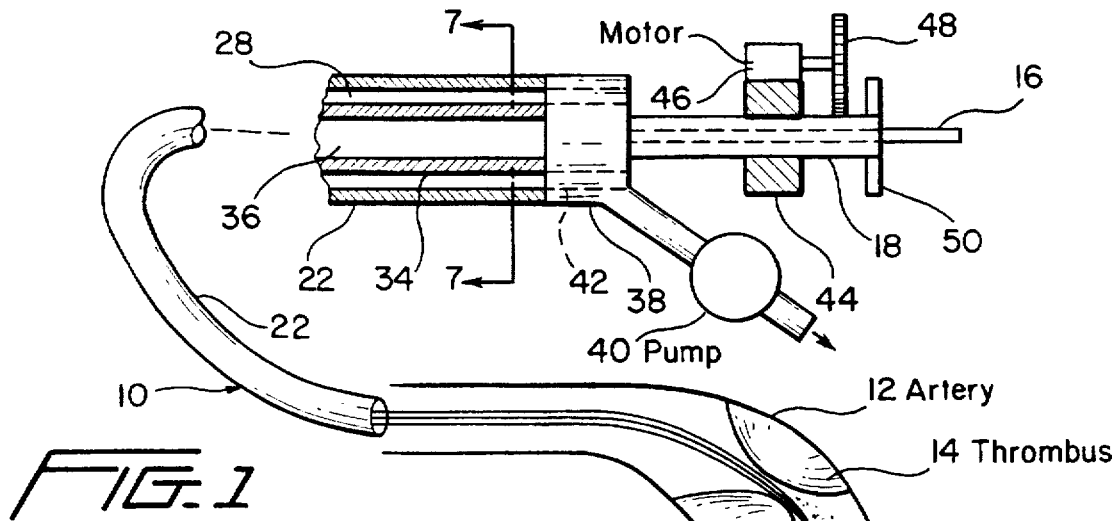
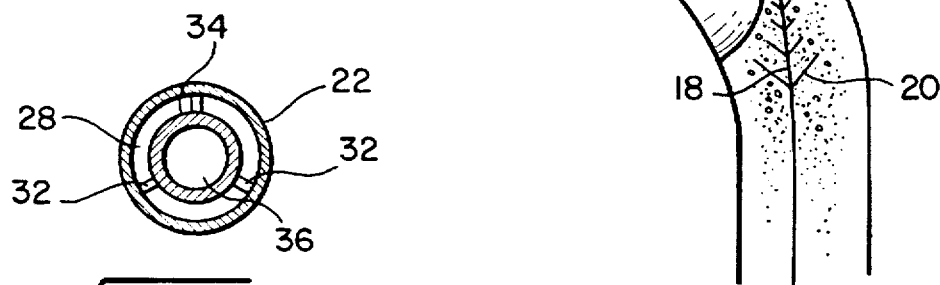
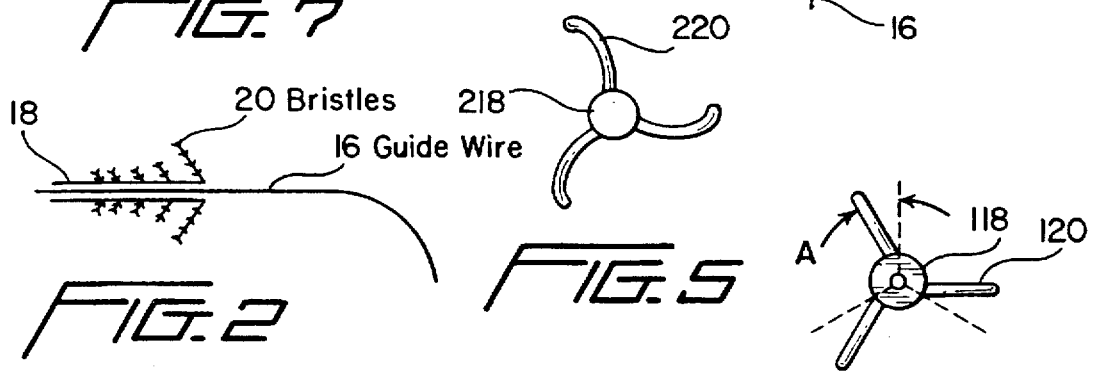
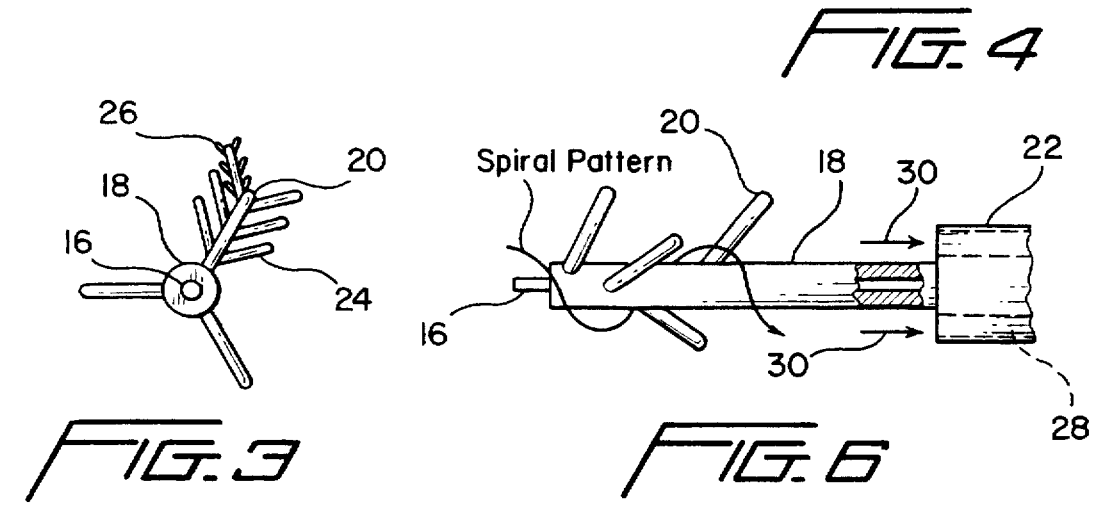

5,895,400

CATHETER WITH BRISTLES

BACKGROUND OF THE INVENTION

The present invention relates to removal of thrombus from arteries. More generally, it relates to a system and method for widening passages in the human body.

Within the human body are various passages which convey fluids. Material may build up on the walls of such passages such that partially blockages may occur. Indeed, such partially blockages may eventually become complete blockages. Whether the blockages are partial or complete, there usually are adverse health consequences.

In the cardiovascular system in particular, a vein or artery may be partially or completely blocked. The veins or venous blood vessels may be blocked (i.e., meaning partially or completely) by a soft blood clot called a thrombus. The arteries or arterial blood vessels may be blocked by a thrombus. In either the vein or artery, plaque or other such blockages should be treated using one or more medical procedures.

The following patents are noted:

| Inventor    | Patent No. | Issue Date        |
|-------------|------------|-------------------|
| Auth        | 4,445,509  | May 1, 1984       |
| Auth        | 4,646,736  | March 3, 1987     |
| Summers     | 4,850,957  | July 25, 1989     |
| Stack et al | 4,867,156  | Sept. 19, 1989    |
| Auth        | 4,990,134  | February 5, 1991  |
| Stack et al | 5,059,211  | October 22, 1991  |
| Stack et al | 5,306,286  | April 26, 1994    |
| Auth et al  | 5,314,407  | May 24, 1994      |
| Auth et al  | 5,364,393  | November 15, 1994 |
| Cragg       | 5,370,653  | December 6, 1994  |

The Stack patents disclose a catheters for removing plaque from the wall of an artery using blade elements and devices to work with such cutting catheters.

The Auth patents show various structures for breaking up thrombus. Diamond dust covered abrasive devices, a cutting tool with spirally shaped cutting flutes, and electrical ablation are among the techniques disclosed.

The Cragg patent and the Summers patent both show cutting catheter systems and methods. Cragg has rotatable soft flexible bristles, whereas Summers has a cutting arrangement with a continuous filament brush and an alternate cutting blade design.

Although the above and other designs may have been somewhat useful, they are often subject to one or more of several disadvantages.

Prior cutting devices often must be sized to fit the particular passage which is being treated. In other words, one must use a different size cutter for different size vessels. Disadvantageously, one must then keep more than one cutter and determine the correct size before putting the cutter into the patient such that the correct size cutter is used. Use of a cutter that is too small does not remove all of the plaque or other built up material. Use of a cutter that is too large increases the chances of damaging healthy tissues on the wall of the passage.

Some prior devices for cutting or removing material from the walls of passages in a patient are constructed such that they may damage healthy tissues on the wall of the passage even if they are the right size. Depending on the characteristics of the blocking material, adjacent healthy tissue, and the cutting device (for example, if the cutting device is too rigid), damage may occur when cutting.

A further problem with some prior arrangements is that materials removed from the wall of a blood vessel for example can create problems downstream from the original blockage. Removed materials can resettle downstream and create a partial or complete blockage at a new location. Depending on the size of material pieces, a heart attack, stroke, or other health problems can result from removing blood vessel obstructing material. Some techniques use chemical solutions to try to dissolve the pieces. Depending on the chemical used, this may require that the passage be blocked by a balloon for a considerable period of time. A catheter controlled balloon may be used downstream from where material is being removed. The balloon prevents removed material from passing by it until the material is dissolved. Suction devices have also been used for removing material.

OBJECTS AND SUMMARY OF THE INVENTION

Accordingly, it is a primary object of the present invention to provide a new and improved catheter system and method.

A more specific object of the present invention is to provide for removal of material from the walls of passages in the body of a patient. Even more specifically, the invention provides for removal of material from the walls of blood vessels.

A further object of the present invention is to provide for removal of material from the walls of passages without requiring a close match between the size of a removing component (which removes material from the wall by cutting, abrading or otherwise) and the size of a passage such as a blood vessel.

Yet another object of the present invention is to provide for removal of material from the walls of passages with little or no risk of damage to body tissues.

A further object of the present invention is to provide for removal of material from the walls of passages with an efficient and simple way of suctioning pieces of removed materials out of the patient's body with minimal risk of damage from removed pieces flowing downstream in a passage. (Some small particles might still go downstream, but not ones sufficiently large, hard or numerous as to cause damage.)

Yet another object of the present invention is to provide for removal of material from the walls of passages quickly.

The above and other features of the present invention which will be more readily understood when the following detailed description is considered in conjunction with the accompanying drawings are realized by a catheter system for widening passages in a patient's body. A guide is extendable into a patient to define a proximal end and a distal end. A member, such as a sweep catheter, has a proximal end and a distal end with a tip. Bristles are attached at the distal end of the sweep catheter such that rotation of the proximal end of the sweep catheter causes rotation of the distal end of the sweep catheter and in turn rotates the bristles such that the bristles are operable to remove material from walls of preexisting passages in the patient. The bristles are inclined away from the tip of the distal end as they extend out from the distal end. (As used herein "inclined" means naturally inclined, i.e., when not stressed by other parts or things.)

More specifically, the catheter system is operable for removing obstructions from the patient's vascular system and the bristles are operable to remove material from walls of passages in the patient's vascular system.

The bristles are distributed over a lengthwise extending portion of the distal end of the sweeper catheter. The bristles extend out variable distances from the distal end of the sweep catheter, the bristles extending further from the distal end of the sweep catheter the closer they are to the tip. (As used herein "extend out variable distances" and "extending further" means naturally, i.e., when not stressed by other parts or things.) Preferably, the bristles are attached to the distal end of the sweep catheter. The bristles extend out at an angle relative to radial lines such that material removed from walls of passages in the patient's vascular system is pushed back in a proximal direction away from the tip by operation of the distal end of the sweep catheter.

The bristles are operable such that material removed from walls of passages in the patient's vascular system is pushed back in a proximal direction away from the tip by operation of the distal end of the sweep catheter. A suction applicator is operable to apply a suction adjacent the distal end of the sweep catheter. A guide catheter is used with a portion of the sweep catheter being inside the guide catheter, the sweep catheter extending out of a distal end of the guide catheter. The suction applicator includes a pump at a proximal end of the guide catheter and a suction channel operably connected to the pump in the guide catheter. The suction is applied adjacent the distal end of the sweep catheter by operation of the pump acting through the suction channel. A rotator is operable to rotate the proximal end of the sweep catheter. A portion of the sweep catheter is inside the guide catheter and the sweep catheter extends out of a distal end of the guide catheter a variable amount.

The present invention may alternately be described as a catheter system for widening passages in the human body including a guide extendable into a patient to define a proximal end and a distal end. The guide is preferably a guide wire. A sweep catheter has a proximal end and a distal end with a tip. Bristles are at the distal end of the sweep catheter, the bristles being rotatable such that the bristles are operable to remove material from walls of preexisting passages in the patient. The bristles are distributed over a lengthwise extending portion of the distal end of the sweeper catheter. The bristles extend out variable distances from the distal end of the sweep catheter, the bristles extending further from the distal end of the sweep catheter the closer they are to the tip. The bristles are attached at the distal end of the sweep catheter such that rotation of the proximal end of the sweep catheter causes rotation of the distal end of the sweep catheter and in turn rotates the bristles such that the bristles are operable to remove material from walls of preexisting passages in the patient.

The catheter system is operable for removing obstructions from the patient's vascular system and the bristles are operable to remove material from walls of passages in the patient's vascular system. The bristles are operable such that material removed from walls of passages in the patient's vascular system is pushed back in a proximal direction away from the tip by operation of the distal end of the sweep catheter. The bristles attached to the distal end of the sweep catheter in turn have sub-bristles mounted thereon. The bristles are naturally inclined away from the tip of the distal end as they extend out from the distal end.

The present invention may also be described as a method of removing material from walls of passages in a patient's vascular system. A guide is extended into the patient's vascular system, the guide having a proximal end and a distal end. A member, such as a sweep catheter having a proximal end and a distal end with a tip, is inserted into the patient along a portion of the guide, the sweep catheter having bristles attached at its distal end. The proximal end of the sweep catheter is rotated to cause rotation of the distal end of the sweep catheter and in turn rotate the bristles such that the bristles remove material from walls of preexisting passages in the patient. Material removed from walls of passages in a patient's vascular system is pushed back in a proximal direction away from the tip by operation of the distal end of the sweep catheter.

The method uses bristles that are inclined away from the tip of the distal end as they extend out from the distal end. The bristles extend out with variable distances from the distal end of the sweep catheter, the bristles extending further from the distal end of the sweep catheter the closer they are to the tip.

The method further includes the step of applying a suction adjacent the distal end of the sweep catheter. A guide catheter is inserted into a patient. The applying of suction uses a pump at a proximal end of the guide catheter and a suction channel operably connected to the pump in the guide catheter. The suction is applied adjacent the distal end of the sweep catheter by operation of the pump acting through the suction channel. The suction channel carries material removed from walls of passages in a patient's vascular system to outside of the patient.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 1 is a simplified side view of a catheter system of the present invention with some portions removed and other parts shown in cross section;

FIG. 2 is a simplified side view of a distal portion of the catheter system;

FIG. 3 is a simplified end view of the distal end of a sweep catheter of the present system;

FIG. 4 is a simplified end view of the distal end of a second embodiment sweep catheter of the present system;

FIG. 5 is a simplified end view of the distal end of a third embodiment sweep catheter;

FIG. 6 is a simplified side view with portions removed of the distal end of the catheter system; and FIG. 7 is a cross section view taken along the lines 7—7 of FIG. 1.

DETAILED DESCRIPTION

Turning initially to FIG. 1, a catheter system 10 according to the present invention is shown partially within a patient's artery 12 in order to remove thrombus 12, which is partially obstructing the artery 12. The catheter system and method of the present invention may also be used for widening other passages in the body of a patient, especially where material has built up or accumulated on the walls of the passage. Obstructions or blockages (as used herein "obstructions" or "blockages" include partial and complete closing of a passage) in different types of passages may be treated. In addition to treating the arteries, other passages in a patient's vascular system, such as veins, may be treated. The discussion which follows will concentrate on the use for removing thrombus from arteries.

The catheter system 10 has a distal end adjacent the thrombus in the patient and a proximal end outside the patient as shown at the top of FIG. 1. The catheter system includes a guide such as guide wire 16, a sweep catheter 18 having bristles 20 (inclined towards the proximal end) on its distal end, and a guide catheter 22. Each of the guide wire 16, sweep catheter 18, and guide catheter 22 have distal ends adjacent where thrombus is to be removed and proximal ends outside of the patient.

As shown in FIGS. 1 and 2, the bristles 20 are distributed over a lengthwise extending portion of the distal end of the sweeper catheter. The bristles extend out variable distances from the distal end of the sweep catheter. Specifically, the bristles 20 extend further from the distal end of the sweep catheter the closer they are to the tip (i.e., distal most point on the guide catheter). As shown in FIGS. 1 and 2, the bristles 20 extend out variable distances from the distal end of the sweep catheter because the bristles adjacent the tip are longer than ones further from the tip. However, all bristles might alternately have the same length, but have different angles relative to the catheter central axis such that they extend out variable distances from the distal end of the sweep catheter.

The guide wire 16 would initially be inserted into the patient until it extends past the partial blockage of thrombus 14. (If a blockage is complete, the guide wire itself may poke through the relatively soft blockage and/or other techniques may be used to bore a hole through the blockage, after which the present technique is used for treating the remaining partial blockage.) The guide catheter 22 is inserted into the patient and along the guide wire 16 (i.e., the guide wire 16 will extend lengthwise through a channel in the guide catheter 22) until the distal end of the guide catheter is seated at the origin of the coronary artery (i.e., right or left main orifice). The sweep catheter 18 may be within the guide catheter 22 when guide catheter 22 is inserted into the patient or may be inserted into the patient after guide catheter insertion. In either case, the sweep catheter 18 extends lengthwise in a channel in the guide catheter 22 and the guide wire 16 is in turn within a channel in sweep catheter 18 as best shown with reference to FIG. 2. The sweep catheter 18 is advanced such that the distal end of sweep catheter 18 with bristles 20 extends at least partially past the narrowest point in the opening through thrombus 14. The inclination of the bristles 20 away from the tip of the distal end of sweep catheter 18 allows the bristles 20 to fold back (not shown) toward the proximal end and parallel or almost parallel to the lengthwise direction of the catheter 18. In other words, as the bristles 20 pass through the narrow part of the opening in thrombus 14, they readily bend to fit through the opening. However, when the bristles 20 are pulled back in the proximal direction, the proximal inclination of bristles 20 tends to keep them from bending back in the distal direction. Basically, the bristles 20 can more freely bend towards their acute angle side (i.e., proximally) than toward their obtuse angle side (i.e., distally). Additionally, the proximal inclination of the bristles 20 allow them to accommodate the size of the artery 12 such that one size may be sufficient (instead of requiring different size heads for different size arteries). Also, the flexibility of the bristles 20 and the portion of the sweep catheter 18 to which they are fixed is such that damage to healthy tissue is avoided or minimized. To that end, the portion of the sweep catheter 18 to which bristles 20 are fixed is preferably normal flexible catheter material.

The sweep catheter 18 is then rotated and pulled back slowly toward the obstruction such that the smaller bristles 20 engage the thrombus 14 first and sweep out the thrombus material enlarging the hole through it. The rotating bristles 20 contacting the thrombus get progressively longer (and extend out progressively further from the distal end of catheter 18) so as to make the hole progressively larger until all or essentially all of the thrombus is removed. The bristles 20 preferably are constructed so as to trap platelets in them similar to the fastening of fabric hook and loop strip fasteners such as sold under the VELCRO trademark. Different materials with different degrees of hardness could be used for the bristles so as to most effectively remove the thrombus with no or minimal damage to the arterial wall. The material used for the bristles may be various plastics or even metal.

In addition or alternately to having the bristles 20 trap the platelets, the guide catheter 22 may have an unshown opening in its distal end for suctioning materials out of the patient through a suction channel in the catheter 22.

With reference to FIGS. 2 and 3, the bristles 20 may include sub-bristles 24 extending out from them and even sub-sub-bristles 26 extending out from the sub-bristles 24. For ease of illustration only a few of the sub-bristles 24 and a few of the sub-sub-bristles 26 are shown. However, it will be understood that all of the bristles 20 may be constructed identically. Additionally, although only three sizes of bristle construction are shown (i.e., bristles, sub-bristles, and sub-sub-bristles), but more different sizes could be used by having the sub-sub-bristles having sub-sub-sub-bristles thereon, etc.

With reference to FIG. 4, an alternate sweep catheter 118 has bristles 120 extending out from the distal end at an angle A relative to the radial lines R. In contrast the FIG. 3 arrangement has the bristles extending in unshown radial lines. Except as discussed, the FIG. 4 sweep catheter 118 would be constructed and operable like catheter 18.

With reference to FIG. 5, an alternate sweep catheter 218 has curved bristles 220 which, like bristles 120 of catheter 118, operate like a corkscrew such that removed thrombus materials are propelled toward the distal end of a guide catheter such as 22 from rotation of the bristles. The guide catheter may then suction materials out of the patient.

With reference to FIG. 6, the sweep catheter 18 may have the bristles 20 arranged in a spiral pattern (i.e., different flights of bristles, like the pattern for a spiral staircase) such that rotation of the bristles 20 tends to pull material in the illustrated spiral path towards the guide catheter 22. The spiral bristle pattern may use the type of bristles illustrated in any of FIGS. 3–5. The materials may be pulled into an annular suction channel 28 in the catheter 22 as illustrated by the arrows 30.

Turning back to the top portion of FIG. 1 and also considering FIG. 7, the proximal end of catheter system 10 will be described. The suction channel 28 has ribs 32 connecting it to tubular wall 34 having central channel 36 therein. The central channel 36 accommodates the guide wire 16 and sweep catheter 18 within it, but those components are not shown within the cross sectioned part of guide catheter 22 for ease of illustration.

An adaptor 38 allows suction pump 40 to apply a suction to the annular channel 28. The adaptor 38 is an end cap with an annular space 42 therein to communicate between the upstream side of pump 40 and the annular channel 28. Additionally, adaptor 38 has a central opening therein to allow the catheter 18 to extend therethrough.

The sweep catheter 18 is rotatably mounted in journal 44 with motor 46 operable to rotate sweep catheter 18 by way of gear or friction wheel 48 coupling to the outer surface of sweep catheter 18. A handle 50 is mounted to the proximal end of catheter 18 for free rotation therebetween. Thus, when a doctor moves the sweep catheter 18 in or out using ring like handle 50, the handle itself will not be rotating from motor 46.

The sweep catheter may more broadly be considered as a flexible member insertable into a patient and having bristles on its distal end. As an alternative to the illustrated designs, the bristles could be located on the guide wire itself and the guide wire could provide the removal by rotation thereof. In that case, such a guide wire may cooperate with the guide catheter 22 either with or without an intermediate catheter within the guide catheter 22. Such an intermediate catheter may include bristles as shown for catheter 18 (in which case, both the guide wire and the catheter may rotate for material removal) or may have no bristles and simply be used for flushing or other purposes.

Although specific constructions have been presented herein, it is to be understood that these are for illustrative purposes only. Various modifications and adaptations will be apparent to those of skill in the art. In view of possible modifications, it will be appreciated that the scope of the present invention should be determined by reference to the claims appended hereto.

What is claimed is:

1. A system for widening passages in the body of a patient comprising:

a member extendable into a patient to define a proximal end and a distal end with a tip;

bristles adjacent the distal end of the member such that rotation of the proximal end of the member causes rotation of the distal end of the member and in turn rotates the bristles such that the bristles are operable to remove material from walls of preexisting passages in the patient; and wherein all of the bristles are inclined away from the tip of the distal end as they extend out from the distal end.

2. The system of claim 1 wherein the system is a catheter system and the member is a sweep catheter with the bristles attached to the distal end thereof; and further comprising a guide extendable into a patient to define a proximal end and a distal end; and wherein the catheter system is operable for removing obstructions from the patient's vascular system and the bristles are operable to remove material from walls of passages in the patient's vascular system.

3. The catheter system of claim 2 wherein the bristles extend out at an angle relative to radial lines such that material removed from walls of passages in the patient's vascular system is pushed back in a proximal direction away from the tip by operation of the distal end of the sweep catheter.

4. The catheter system of claim 3 further comprising a suction applicator operable to apply a suction adjacent the distal end of the sweep catheter.

5. The catheter system of claim 3 further comprising a guide catheter, a portion of the sweep catheter being inside the guide catheter, the sweep catheter extending out of a distal end of the guide catheter; and wherein the suction applicator includes a pump at a proximal end of the guide catheter and a suction channel operably connected to the pump in the guide catheter; and wherein suction is applied adjacent the distal end of the sweep catheter by operation of the pump acting through the suction channel.

6. The catheter system of claim 5 further comprising a rotator operable to rotate the proximal end of the sweep catheter, a portion of the sweep catheter being inside the guide catheter, the sweep catheter extending out of a distal end of the guide catheter.

7. A system for widening passages in the body of a patient comprising:

a member extendable into a patient to define a proximal end and a distal end with a tip; bristles adjacent the distal end of the member such that rotation of the proximal end of the member causes rotation of the distal end of the member and in turn rotates the bristles such that the bristles are operable to remove material from walls of preexisting passages in the patient; and wherein the bristles are inclined away from the tip of the distal end as they extend out from the distal end wherein the system is a catheter system and the member is a sweep catheter with the bristles attached to the distal end thereof; and further comprising a guide extendable into a patient to define a proximal end and a distal end; and wherein the catheter system is operable for removing obstructions from the patient's vascular system and the bristles are operable to remove material from walls of passages in the patient's vascular system; and wherein the bristles are distributed over a lengthwise extending portion of the distal end of the sweeper catheter, wherein the bristles extend out variable distances from the distal end of the sweep catheter, the bristles extending further from the distal end of the sweep catheter the closer they are to the tip.

8. The catheter system of claim 7 wherein the bristles are attached to the distal end of the sweep catheter.

9. The catheter system of claim 8 wherein the bristles extend out at an angle relative to radial lines such that material removed from walls of passages in the patient's vascular system is pushed back in a proximal direction away from the tip by operation of the distal end of the sweep catheter.

10. A catheter system for widening passages in the body of a patient comprising:

a guide extendable into a patient to define a proximal end and a distal end;

a sweep catheter having a proximal end and a distal end with a tip; and bristles at the distal end of the sweep catheter, the bristles being rotatable such that the bristles are operable to remove material from walls of preexisting passages in the patient; and wherein the bristles are distributed over a lengthwise extending portion of the distal end of the sweeper catheter, wherein the bristles extend out variable distances from the distal end of the sweep catheter, the bristles extending further from the distal end of the sweep catheter the closer they are to the tip.

11. The catheter system of claim 10 wherein the bristles are attached at the distal end of the sweep catheter such that rotation of the proximal end of the sweep catheter causes rotation of the distal end of the sweep catheter and in turn rotates the bristles such that the bristles are operable to remove material from walls of preexisting passages in the patient.

12. The catheter system of claim 11 wherein the catheter system is operable for removing obstructions from the patient's vascular system and the bristles are operable to remove material from walls of passages in the patient's vascular system.

13. The catheter system of claim 12 wherein the bristles are operable such that material removed from walls of passages in the patient's vascular system is pushed back in a proximal direction away from the tip by operation of the distal end of the sweep catheter.

14. The catheter system of claim 13 wherein the bristles attached to the distal end of the sweep catheter in turn have sub-bristles mounted thereon.

15. The catheter system of claim 13 wherein the bristles are inclined away from the tip of the distal end as they extend out from the distal end.

16. A method of removing material from walls of passages in a patient's vascular system, the steps comprising:

extending a member into the patient's vascular system, the member having a proximal end and a distal end with a tip in the patient, the member having bristles attached at its distal end; and rotating the proximal end of the member to cause rotation of the distal end of the member and in turn rotate the bristles such that the bristles remove material from walls of preexisting passages in the patient; and wherein material removed from walls of passages in a patient's vascular system is pushed back in a proximal direction away from the tip by operation of the distal end of the member.

17. The method of claim 16 using bristles that are inclined away from the tip of the distal end as they extend out from the distal end.

18. The method of claim 16 using bristles that are inclined away from the tip of the distal end as they extend out from the distal end.

19. The method of claim 16 further comprising the step of applying a suction adjacent the distal end of the sweep catheter.

20. The method of claim 19 further comprising the step of: prior to inserting the member, extending a guide having a proximal end and a distal end into the patient's vascular system; and wherein the member is a sweep catheter inserting to extend along a portion of the guide, the sweep catheter having bristles attached at its distal end; and further comprising the step of inserting a guide catheter into a patient; and wherein the applying of suction uses a pump at a proximal end of the guide catheter and a suction channel operably connected to the pump in the guide catheter; and wherein suction is applied adjacent the distal end of the sweep catheter by operation of the pump acting through the suction channel; and wherein the suction channel carries material removed from walls of passages in a patient's vascular system to outside of the patient.

* * * * *